United States Patent
Ayal et al.

(10) Patent No.: US 7,627,384 B2
(45) Date of Patent: Dec. 1, 2009

(54) TECHNIQUES FOR NERVE STIMULATION

(75) Inventors: Shai Ayal, Jerusalem (IL); Ehud Cohen, Ganei Tikva (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 656 days.

(21) Appl. No.: 11/280,884

(22) Filed: Nov. 15, 2005

(65) Prior Publication Data

US 2006/0106441 A1   May 18, 2006

Related U.S. Application Data

(60) Provisional application No. 60/628,391, filed on Nov. 15, 2004.

(51) Int. Cl.
*A61N 1/08* (2006.01)
(52) U.S. Cl. ..................................... 607/118
(58) Field of Classification Search ................. 607/118
See application file for complete search history.

(56) References Cited

U.S. PATENT DOCUMENTS

| | | | |
|---|---|---|---|
| 3,411,507 A | 11/1968 | Wingrove |
| 4,019,518 A | 4/1977 | Maurer et al. |
| 4,161,952 A | 7/1979 | Kinney et al. |
| 4,338,945 A | 7/1982 | Kosugi et al. |
| 4,392,496 A | 7/1983 | Stanton |
| 4,535,785 A | 8/1985 | van den Honert et al. |
| 4,559,948 A | 12/1985 | Liss et al. |
| 4,573,481 A | 3/1986 | Bullara |
| 4,585,005 A | 4/1986 | Lue et al. |
| 4,602,624 A | 7/1986 | Naples et al. |
| 4,608,985 A | 9/1986 | Crish et al. |
| 4,628,942 A | 12/1986 | Sweeney et al. |
| 4,632,116 A | 12/1986 | Rosen et al. |
| 4,649,936 A | 3/1987 | Ungar et al. |
| 4,663,102 A | 5/1987 | Brenman et al. |
| 4,702,254 A | 10/1987 | Zabara |
| 4,739,764 A | 4/1988 | Lue et al. |
| 4,867,164 A | 9/1989 | Zabara |
| 4,926,865 A | 5/1990 | Oman |
| 4,962,751 A | 10/1990 | Krauter |

(Continued)

FOREIGN PATENT DOCUMENTS

EP    0 688 577    12/1995

(Continued)

OTHER PUBLICATIONS

Office Action issued Jun. 27, 2008 during the prosecution of Applicants' U.S. Appl. No. 10/205,475.

(Continued)

*Primary Examiner*—Mark W Bockelman
*Assistant Examiner*—Eric D Bertram
(74) *Attorney, Agent, or Firm*—John P. White; Cooper & Dunham LLP

(57) ABSTRACT

Apparatus is provided for applying current to a nerve, including a housing, adapted to be placed in a vicinity of the nerve, and at least one cathode and at least one anode, fixed to the housing. The apparatus further includes two or more passive electrodes, fixed to the housing, and a conducting element, which electrically couples the passive electrodes to one another. Other embodiments are also described.

9 Claims, 3 Drawing Sheets

U.S. PATENT DOCUMENTS

| | | |
|---|---|---|
| 5,025,807 A | 6/1991 | Zabara |
| 5,042,497 A | 8/1991 | Shapland |
| 5,069,680 A | 12/1991 | Grandjean |
| 5,170,802 A | 12/1992 | Mehra |
| 5,178,161 A | 1/1993 | Kovacs |
| 5,188,104 A | 2/1993 | Wernicke et al. |
| 5,199,428 A | 4/1993 | Obel et al. |
| 5,199,430 A | 4/1993 | Fang et al. |
| 5,203,326 A | 4/1993 | Collins |
| 5,205,285 A | 4/1993 | Baker, Jr. |
| 5,215,086 A | 6/1993 | Terry, Jr. et al. |
| 5,224,491 A | 7/1993 | Mehra |
| 5,243,980 A | 9/1993 | Mehra |
| 5,263,480 A | 11/1993 | Wernicke et al. |
| 5,282,468 A | 2/1994 | Klepinski |
| 5,292,344 A | 3/1994 | Douglas |
| 5,299,569 A | 4/1994 | Wernicke et al. |
| 5,314,495 A | 5/1994 | Kovacs |
| 5,330,507 A | 7/1994 | Schwartz |
| 5,334,221 A | 8/1994 | Bardy |
| 5,335,657 A | 8/1994 | Terry, Jr. et al. |
| 5,356,425 A | 10/1994 | Bardy et al. |
| 5,411,531 A | 5/1995 | Hill et al. |
| 5,423,872 A | 6/1995 | Cigaina |
| 5,437,285 A | 8/1995 | Verrier et al. |
| 5,439,938 A | 8/1995 | Snyder et al. |
| 5,454,840 A | 10/1995 | Krakovsky et al. |
| 5,487,756 A * | 1/1996 | Kallesoe et al. ............. 607/118 |
| 5,507,784 A | 4/1996 | Hill et al. |
| 5,522,854 A | 6/1996 | Ideker et al. |
| 5,540,730 A | 7/1996 | Terry, Jr. et al. |
| 5,540,734 A | 7/1996 | Zabara |
| 5,562,718 A | 10/1996 | Palermo |
| 5,571,150 A | 11/1996 | Wernicke et al. |
| 5,578,061 A | 11/1996 | Stroetmann et al. |
| 5,634,462 A | 6/1997 | Tyler et al. |
| 5,645,570 A | 7/1997 | Corbucci |
| 5,658,318 A | 8/1997 | Stroetmann et al. |
| 5,690,681 A | 11/1997 | Geddes et al. |
| 5,690,691 A | 11/1997 | Chen et al. |
| 5,700,282 A | 12/1997 | Zabara |
| 5,707,400 A | 1/1998 | Terry, Jr. et al. |
| 5,711,316 A | 1/1998 | Elsberry et al. |
| 5,716,385 A | 2/1998 | Mittal et al. |
| 5,755,750 A | 5/1998 | Petruska et al. |
| 5,824,027 A | 10/1998 | Hoffer et al. |
| 5,832,932 A | 11/1998 | Elsberry et al. |
| 5,833,709 A | 11/1998 | Rise et al. |
| 5,836,994 A | 11/1998 | Bourgeois |
| 5,916,239 A | 6/1999 | Geddes et al. |
| 5,938,584 A | 8/1999 | Ardito et al. |
| 5,938,596 A | 8/1999 | Woloszko et al. |
| 6,006,134 A | 12/1999 | Hill et al. |
| 6,026,326 A | 2/2000 | Bardy |
| 6,058,331 A | 5/2000 | King |
| 6,066,163 A | 5/2000 | John |
| 6,073,048 A | 6/2000 | Kieval et al. |
| 6,086,525 A | 7/2000 | Davey et al. |
| 6,091,977 A | 7/2000 | Tarjan et al. |
| 6,091,992 A | 7/2000 | Bourgeois et al. |
| 6,094,598 A | 7/2000 | Elsberry et al. |
| 6,097,984 A | 8/2000 | Douglas |
| 6,104,955 A | 8/2000 | Bourgeois |
| 6,104,960 A | 8/2000 | Duysens et al. |
| 6,119,516 A | 9/2000 | Hock |
| H1905 H | 10/2000 | Hill |
| 6,134,470 A | 10/2000 | Hartlaub |
| 6,146,335 A | 11/2000 | Gozani |
| 6,161,029 A | 12/2000 | Spreigl et al. |
| 6,167,304 A | 12/2000 | Loos |
| 6,169,924 B1 | 1/2001 | Meloy et al. |
| 6,205,359 B1 | 3/2001 | Boveja |
| 6,230,061 B1 | 5/2001 | Hartung |
| 6,240,314 B1 | 5/2001 | Picchi et al. |
| 6,266,564 B1 | 7/2001 | Hill et al. |
| 6,272,377 B1 | 8/2001 | Sweeney et al. |
| 6,292,695 B1 | 9/2001 | Webster, Jr. et al. |
| 6,319,241 B1 | 11/2001 | King et al. |
| 6,341,236 B1 | 1/2002 | Osorio et al. |
| 6,356,784 B1 | 3/2002 | Lozano et al. |
| 6,366,813 B1 | 4/2002 | DiLorenzo |
| 6,381,499 B1 | 4/2002 | Taylor et al. |
| 6,400,982 B2 | 6/2002 | Sweeney et al. |
| 6,405,079 B1 | 6/2002 | Ansarinia |
| 6,434,424 B1 | 8/2002 | Igel et al. |
| 6,449,507 B1 | 9/2002 | Hill et al. |
| 6,456,866 B1 | 9/2002 | Tyler et al. |
| 6,463,328 B1 | 10/2002 | John |
| 6,473,644 B1 | 10/2002 | Terry, Jr. et al. |
| 6,493,585 B2 | 12/2002 | Plicchi et al. |
| 6,511,500 B1 | 1/2003 | Rahme |
| 6,542,774 B2 | 4/2003 | Hill et al. |
| 6,564,096 B2 | 5/2003 | Mest |
| 6,587,727 B2 | 7/2003 | Osorio et al. |
| 6,600,956 B2 | 7/2003 | Maschino et al. |
| 6,610,713 B2 | 8/2003 | Tracey |
| 6,628,987 B1 | 9/2003 | Hill et al. |
| 6,668,191 B1 | 12/2003 | Boveja |
| 6,671,556 B2 | 12/2003 | Osorio et al. |
| 6,684,105 B2 | 1/2004 | Cohen et al. |
| RE38,705 E | 2/2005 | Hill et al. |
| 6,865,416 B2 | 3/2005 | Dev et al. |
| 6,895,280 B2 | 5/2005 | Meadows et al. |
| 6,907,295 B2 | 6/2005 | Gross et al. |
| 6,928,320 B2 | 8/2005 | King |
| 6,934,583 B2 | 8/2005 | Weinberg et al. |
| 6,985,774 B2 | 1/2006 | Kieval et al. |
| 7,050,846 B2 | 5/2006 | Sweeney et al. |
| 7,076,299 B2 | 7/2006 | Thong |
| 7,076,307 B2 | 7/2006 | Boveja et al. |
| 2002/0035335 A1 | 3/2002 | Schauerte |
| 2002/0107553 A1 | 8/2002 | Hill et al. |
| 2002/0120304 A1 | 8/2002 | Mest |
| 2003/0018367 A1 | 1/2003 | DiLorenzo |
| 2003/0040774 A1 | 2/2003 | Terry, Jr. et al. |
| 2003/0045909 A1 | 3/2003 | Gross et al. |
| 2003/0050677 A1 | 3/2003 | Gross et al. |
| 2003/0078623 A1 | 4/2003 | Weinberg et al. |
| 2003/0097221 A1 | 5/2003 | Chun et al. |
| 2003/0100924 A1 | 5/2003 | Foreman et al. |
| 2003/0195574 A1 | 10/2003 | Osorio et al. |
| 2003/0216775 A1 | 11/2003 | Hill et al. |
| 2003/0229380 A1 | 12/2003 | Adams et al. |
| 2003/0233129 A1 | 12/2003 | Matos |
| 2003/0236558 A1 | 12/2003 | Whitehurst et al. |
| 2004/0048795 A1 | 3/2004 | Ivanova et al. |
| 2004/0059392 A1 | 3/2004 | Parramon et al. |
| 2004/0138721 A1 | 7/2004 | Osorio et al. |
| 2004/0152958 A1 | 8/2004 | Frei et al. |
| 2004/0158119 A1 | 8/2004 | Osorio et al. |
| 2004/0162594 A1 | 8/2004 | King |
| 2004/0172075 A1 | 9/2004 | Shafer et al. |
| 2004/0199210 A1 | 10/2004 | Shelchuk |
| 2004/0215289 A1 | 10/2004 | Fukui |
| 2004/0243182 A1 | 12/2004 | Cohen et al. |
| 2004/0249416 A1 | 12/2004 | Yun et al. |
| 2005/0038490 A1 | 2/2005 | Gross et al. |
| 2005/0131467 A1 | 6/2005 | Boveja |
| 2005/0187584 A1 | 8/2005 | Denker et al. |
| 2005/0222644 A1 | 10/2005 | Killian et al. |
| 2006/0015153 A1 | 1/2006 | Gliner et al. |
| 2006/0030919 A1 | 2/2006 | Mrva et al. |
| 2006/0052831 A1 | 3/2006 | Fukui |
| 2006/0074450 A1 | 4/2006 | Boveja et al. |

| | | | |
|---|---|---|---|
| 2006/0129205 A1 | 6/2006 | Boveja et al. | |
| 2006/0136024 A1 | 6/2006 | Cohen et al. | |
| 2006/0195170 A1 | 8/2006 | Cohen et al. | |
| 2006/0282145 A1 | 12/2006 | Caparso et al. | |

FOREIGN PATENT DOCUMENTS

| | | |
|---|---|---|
| EP | 0 831 954 | 12/1996 |
| WO | WO 01/10375 | 2/2001 |
| WO | WO 01/10432 | 2/2001 |
| WO | WO 01/26729 | 4/2001 |
| WO | WO 02/085448 | 10/2002 |

OTHER PUBLICATIONS

Fang, Zi-Ping and Mortimer, J. Thomas, (1991) "Selective activation of small motor axons by quasitrapezoidal current pulses," *IEEE Transactions on Biomedical Engineering*, 38(2):168-174.

An Office Action dated Nov. 1, 207, which issued during the prosecution of Applicant's U.S. Appl. No. 10/205,475.

Jones, et al., "Heart rate responses to selective stimulation of cardiac vagal C fibres in anaesthetized cats, rats and rabbits", Journal of Physiology (1995), 489.1 pp. 203-214.

Jones, et al., "Activity of C fibre cardiac vagal efferents in anaesthetized cats and rats", Journal of Physiology (1998), 507.3, pp. 869-880.

Baratta, R. et al., (1989) "Orderly stimulation of skeletal muscle motor units with tripolar nerve cuff electrode," *IEEE Transactions on Biomedical Engineering*, 36(1): 836-843.

Deurloo, K.E. et al., (1998) "Transverse tripolar stimulation of peripheral nerve: a modeling study of spatial selectivity," *Med. Bio. Eng. Comput.*, 36: 66-74.

Evans, M.S. et al., (2004) "Intraoperative human vagus nerve compound action potentials," *Acta. Neurol. Scand.*, 110: 232-238.

Fitzpatrick, D.M. et al., (1991) "A nerve cuff design for the selective activation and blocking of myelinated nerve fibers," *Ann. Intl. Conf of the IEEE Eng. In Med. and Bio.*, 13(2): 906-907.

Goodall, E.V. et al., (1996) "Position-selective activation of peripheral nerve fibers with a cuff electrode," *IEEE Transactions on Biomedical Engineering*, 43(8): 851-856.

Grill, W.M. et al., (1997) "Inversion of the current-distance relationship by transient depolarization," *IEEE Transactions on Biomedical Engineering*, 44(1): 1-9.

Jones, J.F.X. et al., (1995) "Heart rate responses to selective stimulation of cardiac vagal C fibres in anaesthetized cats, rats and rabbits," *J. Physiol.*, 489(Pt. 1): 203-211.

Lertamanorat, Z. et al., (2004) "A novel electrode array for diameter-dependent control of axonal excitability: a simulation study," *IEEE Trans. Bio. Eng.*, 51(7): 1242-1250.

Mushahwar, V.K. et al., (2000) "Muscle recruitment through electrical stimulation of the lumbo-sacral spinal cord," *IEEE Transactions on Biomedical Engineering*, 8(1): 22-29.

Naples, G.G. et al., (1988) "A spiral nerve cuff electrode for peripheral nerve stimulation," *IEEE Transactions on Biomedical Engineering*, 35(11): 905-916.

Rattay, F., (1989) "Analysis of models for extracellular fiber stimulation," *IEEE Trans. Bio. Eng.*, 36(2): 676-682.

Rijkhoff, N. J. et al., (1994) "Acute animal studies on the use of anodal block to reduce urethral resistance in sacral root stimulation," *IEEE Transactions on Rehabilitation Engineering*, 2(2): 92-99.

Rijkhoff, N. J. et al., (1998) "Orderly recruitment of motoneurons in an acute rabbit model," *Proc. of the Annual Conf of the IEEE Engineering in Medicine and Biology Society*, 20(5): 2564-2565.

Sweeney, J.D. et al., (1990) "An asymmetric two electrode cuff for generation of unidirectionally propagated action potentials," *IEEE Transactions on Biomedical Engineering*, BME-33(6): 541-549.

Sweeney, J.D. et al., (1986) "A nerve cuff technique for selective excitation of peripheral nerve trunk regions," *IEEE Transactions on Biomedical Engineering*, 37(7): 706-715.

Tarver, W.B. et al., (1992) "Clinical experience with a helical bipolar stimulating lead," *Pace*: vol. 15, Oct., Part II: 1545-1556.

Ungar, I.J. et al., (1986) "Generation of unidirectionally propagating action potentials using a monopolar electrode cuff," *Annals of Biomedical Engineering*, 14: 437-450.

Van Den Honert, C. et al., (1981) "A technique for collision block of peripheral nerve: Frequency dependence," *MP-12, IEEE Transactions on Biomedical Engineering*: 28: 379-382.

Van Den Honert, C. et al., (1979) "Generation of unidirectionally propagated action potentials in a peripheral nerve by brief stimuli," *Science: 206*: 1311-1312.

Veraart, C. et al., (1993) "Selective control of muscle activation with a multipolar nerve cuff electrode," *IEEE Transactions on Biomedical Engineering*, 40(7): 640-653.

Bibevski, S., et al., "Ganglionic Mechanisms Contribute to Diminished Vagal Control in Heart Failure," *Circulation* 99:2958-2963 (1999).

Bilgutay, A., et al., "Vagal tuning a new concept in the treatment of supraventricular arrhythmias, angina pectoris, and heart failure," *J. Thoracic Cardiovasc. Surg.* 56(1): 71- 82 (1968).

Bluemel, K.M., et al., "Parasympathetic postganglionic pathways to the sinoatrial node," *Am. J. Physiol.* 259 (Heart Circ. Physiol. 28):H1504-1510 (1990).

Carlson, M.D., et al., "Selective stimulation of parasympathetic nerve fibers to the human sinoatrial node," *Circulation* 85:1311-1317 (1992).

Chen, S.A., et al., "Intracardiac Stimulation of Human Parasympathetic Nerve Fibers Induces Negative Dromotropic Effects: Implication with the Lesions of Radiofrequency Catheter Ablation," *J. Cardiovasc. Electrophysiol.* 9(3):245- 252 (1998).

Cooper, T.B., et al., "Neural effects on sinus rate and atrioventricular conduction produced by electrical stimulation from a transvenous electrode catheter in the canine right pulmonary artery," *Circ. Res.* 46(1):48-57 (1980).

Cummings, J.E. et al., "Preservation of the Anterior Fat Pad Paradoxically Decreases the Incidence of Postoperative Atrial Fibrillation in Humans," *J. Am. Coll. Cardiol.* 43(6):994-1000 (2004).

Friedrichs, G., "Experimental models of atrial fibrillation/flutter", *J. Pharmacol. and Toxicol. Methods* 43:117-123 (2000).

Furukawa, Y., et al., "Differential Blocking Effects of Atropine and Gallamine on Negative Chronotropic and Dromotropic Responses to Vagus Stimulation in Anesthetized Dogs," *J. Pharmacol. & Exper. Therapeut.* 251(3):797-802 (1989).

Fuster, V. and Ryden, L.E., et al., "ACC/AHA/ESC Guidelines for the Management of Patients With Atrial Fibrillation," *J. Am. Coll. Cardiol.* 38(4):1266i-lxx (2001).

Garrigue, S., et al., "Post-Ganglionic Vagal Stimulation of the Atrioventricular Node Reduces Ventricular Rate during Atrial Fibrillation," *PACE* 21(4) Part II: 878 (1998).

Goldberger, J.J., et al., "New technique for vagal nerve stimulation," *J. Neurosci. Methods* 91:109-114 (1999).

Hjalmarson, A., "Prevention of Sudden Cardiac Death with Beta Blockers", *Clin. Cardiol.* 22(Supp. V): V-11-V-15 (1999).

Jideus, L., "Atrial Fibrillation after Coronary Artery Bypass Surgery," *Acta Universitatis Upsaliensis*: Comprehensive Summaries of Uppsala Dissertations from the Faculty of Medicine 1093:1-56 (2001).

Kwan, H., et al., "Cardiovascular Adverse Drug Reactions during Initiation of Antiarrhythmic Therapy for Atrial Fibrillation," *Can. J. Hosp. Pharm.* 54:10-14 (2001).

Li, D., et al., "Promotion of Atrial Fibrillation by Heart Failure in Dogs," *Circulation* 100:87-95 (1999).

Manfredi, M., "Differential Block of Conduction of Larger Fibers in Peripheral Nerve by Direct Current," *Arch. Ital. Biol.* 108:52-71 (1970).

Mazgalev, T.N., "AV Nodal Physiology," *Heart Rhythm Society* (www.hrsonline.org) (no date).

Pagé, P.L., et al., "Regional distribution of atrial electrical changes induced by stimulation of extracardiac and intracardiac neural elements," *J. Thorac. Cardiovasc. Surg.* 109:377-88 (1995).

Rijkhoff, N.J.M and Sinkjær, T., "Selective Stimulation of Small Diameter Nerve Fibers in a Mixed Bundle", *Proceedings of the Annual Project Meeting Sensations/Neuros and Mid Term Review Meeting Neuros*, Apr. 21-23, 1999:20-21 (1999).

Waninger, M.S., et al., "Electrophysiological Control of Ventricular Rate During Atrial Fibrillation," *PACE* 23:1239-1244 (2000).

Zhang, Y. et al., "Optimal ventricular rate slowing during atrial fibrillation by feedback AV nodal-selective vagal stimulation," *Am. J. Physiol. Heart Circ. Physiol.* 282:H1102-H1110 (2002).

European Office Action issued by the European Patent Office in connection with European Application No. 06255816.8, dated May 25, 2009 (Biocontrol Medical Ltd.).

* cited by examiner

TECHNIQUES FOR NERVE STIMULATION

CROSS-REFERENCES TO RELATED APPLICATIONS

The present patent application claims the benefit of U.S. Provisional Patent Application 60/628,391, filed Nov. 15, 2004, which is assigned to the assignee of the present application and is incorporated herein by reference.

FIELD OF THE INVENTION

The present invention relates generally to electrical stimulation of tissue, and specifically to methods and devices for regulating the stimulation of nerves.

BACKGROUND OF THE INVENTION

In the body, axons are grouped together for most of their lengths in nerve bundles. In a single bundle, many different axons travel together, branching only near their target organs. Important properties of natural axonal activity include that: (a) each axon can fire independently of its neighbors in the bundle, and (b) each axon conveys action potentials in only one direction, either afferently (towards the brain) or efferently (towards its target organ). These two properties, however, are not properties of the axons themselves. The axons are only active cables emanating from neurons which can trigger action potentials in them. Since each axon can be connected to a different neuron, they can fire independently. Also, because the axons are connected to a neuron only on one side, they only convey action potentials away from the neuron.

When axons are activated artificially by simple stimulation of a nerve bundle, both of these properties of natural axonal activity are lost: entire regions of the bundle are activated simultaneously, and the axons fire in both directions at once, since the action potential is not triggered at only one of the ends of the axons. The loss of these properties causes the effect of artificial stimulation to be less natural, and may result in side effects, because axons in the bundle in addition to the target axon are indiscriminately activated. To overcome these shortcomings of simple stimulation, two stimulation techniques have been developed: selective stimulation and unidirectional stimulation.

Selective electrical stimulation of nerve fibers is the activation of small fibers in a nerve bundle without the activation of the large fibers. This is advantageous, for example, when the target organ is innervated only by small fibers. In addition, stimulation of large fibers can cause unwanted side effects (see, for example, Rijkhoff et al. (1994) and Jones J F et al., cited hereinbelow). Often, in addition to selective stimulation, it is also advantageous to stimulate unidirectionally such that only organs at one end of the nerve receive signals.

As defined by Rattay, in the article, "Analysis of models for extracellular fiber stimulation," IEEE Transactions on Biomedical Engineering, Vol. 36, no. 2, p. 676, 1989, which is incorporated herein by reference, the activation function (AF) of an unmyelinated axon is the second spatial derivative of the electric potential along an axon. In the region where the activation function is positive, the axon depolarizes, and in the region where the activation function is negative, the axon hyperpolarizes. If the activation function is sufficiently positive, then the depolarization will cause the axon to generate an action potential; similarly, if the activation function is sufficiently negative, then local blocking of action potentials transmission occurs. The activation function depends on the current applied, as well as the geometry of the electrodes and of the axon.

For a given electrode geometry, the equation governing the electrical potential is:

$$\nabla(\sigma \nabla U) = 4\pi j,$$

where U is the potential, σ is the conductance tensor specifying the conductance of the various materials (electrode housing, axon, intracellular fluid, etc.), and j is a scalar function representing the current source density specifying the locations of current injection. The activation function is found by solving this partial differential equation for U. If an unmyelinated axon is defined to lie in the z direction, then the activation function is:

$$AF = \frac{\partial^2 U}{\partial z^2}.$$

In a simple, illustrative example of a point electrode located a distance d from the axis of an axon in a uniformly-conducting medium with conductance σ, the two equations above are solvable analytically, to yield:

$$AF = \frac{I_{el}}{4\pi\sigma} \cdot \frac{2z^2 - d^2}{(z^2 + d^2)^{2.5}},$$

where $I_{el}$ is the electrode current. It is seen that when σ and d are held constant, and for a constant positive $I_{el}$ (to correspond to anodal current), the minimum value of the activation function is negative, and is attained at z=0, i.e., at the point on the nerve closest to the source of the anodal current. Thus, the most negative point on the activation function corresponds to the place on a nerve where hyperpolarization is maximized, namely at the point on the nerve closest to the anode.

Additionally, this equation predicts positive "lobes" for the activation function on either side of z=0, these positive lobes peaking in their values at a distance which is dependent on each of the other parameters in the equation. The positive values of the activation function correspond to areas of depolarization, a phenomenon typically associated with cathodic current, not anodal current. However, it has been shown that excess anodal current does indeed cause the generation of action potentials adjacent to the point on a nerve corresponding to z=0, and this phenomenon is therefore called the "virtual cathode effect." (An analogous, but reverse phenomenon, the "virtual anode effect" exists responsive to excess cathodic stimulation.)

The Rattay article also describes techniques for calculating the activation function for nerves containing myelinated axons. The activation function in this case varies as a function of the diameter of the axon in question. Thus, the activation function calculated for a 1 micron diameter myelinated axon is different from the activation function calculated for a 10 micron diameter axon.

U.S. Pat. No. 6,684,105 to Cohen et al., which is assigned to the assignee of the present application and is incorporated herein by reference, describes apparatus comprising an electrode device adapted to be coupled to longitudinal nervous tissue of a subject, and a control unit adapted to drive the electrode device to apply to the nervous tissue a current which is capable of inducing action potentials that propagate in the nervous tissue in a first direction, so as to treat a condition.

The control unit is further adapted to suppress action potentials from propagating in the nervous tissue in a second direction opposite to the first direction.

U.S. Pat. No. 6,907,295 to Gross et al., which is assigned to the assignee of the present application and is incorporated herein by reference, describes apparatus for applying current to a nerve. A cathode is adapted to be placed in a vicinity of a cathodic longitudinal site of the nerve and to apply a cathodic current to the nerve. A primary inhibiting anode is adapted to be placed in a vicinity of a primary anodal longitudinal site of the nerve and to apply a primary anodal current to the nerve. A secondary inhibiting anode is adapted to be placed in a vicinity of a secondary anodal longitudinal site of the nerve and to apply a secondary anodal current to the nerve, the secondary anodal longitudinal site being closer to the primary anodal longitudinal site than to the cathodic longitudinal site.

A number of patents and articles describe methods and devices for stimulating nerves to achieve a desired effect. Often these techniques include a design for an electrode or electrode cuff.

U.S. Pat. No. 4,608,985 to Crish et al. and U.S. Pat. No. 4,649,936 to Ungar et al., which are incorporated herein by reference, describe electrode cuffs for selectively blocking orthodromic action potentials passing along a nerve trunk, in a manner intended to avoid causing nerve damage.

PCT Patent Publication WO 01/10375 to Felsen et al., which is incorporated herein by reference, describes apparatus for modifying the electrical behavior of nervous tissue. Electrical energy is applied with an electrode to a nerve in order to selectively inhibit propagation of an action potential.

U.S. Pat. No. 5,755,750 to Petruska et al., which is incorporated herein by reference, describes techniques for selectively blocking different size fibers of a nerve by applying direct electric current between an anode and a cathode that is larger than the anode.

U.S. Pat. No. 5,824,027 Hoffer et al., which is incorporated herein by reference, describes a nerve cuff having one or more sets of electrodes for selectively recording electrical activity in a nerve or for selectively stimulating regions of the nerve. Each set of electrodes is located in a longitudinally-extending chamber between a pair of longitudinal ridges which project into the bore of the nerve cuff. The ridges are electrically insulating and serve to improve the selectivity of the nerve cuff. The ridges seal against an outer surface of the nerve without penetrating the nerve. In an embodiment, circumferential end sealing ridges extend around the bore at each end of the longitudinal ridges, and are described as enhancing the electrical and/or fluid isolation between different ones of the longitudinally-extending chambers.

U.S. Pat. No. 4,628,942 to Sweeney et al., which is incorporated herein by reference, describes an annular electrode cuff positioned around a nerve trunk for imposing electrical signals on to the nerve trunk for the purpose of generating unidirectionally propagated action potentials. The electrode cuff includes an annular cathode having a circular passage therethrough of a first diameter. An annular anode has a larger circular passage therethrough of a second diameter, which second diameter is about 1.2 to 3.0 times the first diameter. A non-conductive sheath extends around the anode, cathode, and nerve trunk. The anode and cathode are placed asymmetrically to one side of the non-conductive sheath.

U.S. Pat. No. 5,423,872 to Cigaina, which is incorporated herein by reference, describes a process for treating obesity and syndromes related to motor disorders of the stomach of a patient. The process consists of artificially altering, by means of sequential electrical pulses and for preset periods of time, the natural gastric motility of the patient to prevent emptying or to slow down gastric transit. The '872 patent describes an electrocatheter adapted to be coupled to a portion of the stomach. A portion of the electrocatheter has a rough surface for producing a fibrous reaction of the gastric serosa, in order to contribute to the firmness of the anchoring.

U.S. Pat. No. 4,573,481 to Bullara, which is incorporated herein by reference, describes an implantable helical electrode assembly, configured to fit around a nerve, for electrically triggering or measuring an action potential or for blocking conduction in nerve tissue. A tissue-contacting surface of each electrode is roughened to increase the electrode surface area.

The following patents, which are incorporated herein by reference, may be of interest:
U.S. Pat. No. 6,230,061 to Hartung
U.S. Pat. No. 5,282,468 to Klepinski
U.S. Pat. No. 4,535,785 to van den Honert et al.
U.S. Pat. No. 5,215,086 to Terry et al.
U.S. Pat. No. 6,341,236 to Osorio et al.
U.S. Pat. No. 5,487,756 to Kallesoe et al.
U.S. Pat. No. 5,634,462 to Tyler et al.
U.S. Pat. No. 6,456,866 to Tyler et al.
U.S. Pat. No. 4,602,624 to Naples et al.
U.S. Pat. No. 6,600,956 to Maschino et al.
U.S. Pat. No. 5,199,430 to Fang et al.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33 (6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92-99 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Hoffer J A et al., "How to use nerve cuffs to stimulate, record or modulate neural activity," in Neural Prostheses for Restoration of Sensory and Motor Function, Chapin J K et al. (Eds.), CRC Press (1st edition, 2000)

Jones J F et al., "Heart rate responses to selective stimulation of cardiac vagal C fibres in anaesthetized cats, rats and rabbits," J Physiol 489 (Pt 1):203-14 (1995)

Evans M S et al., "Intraoperative human vagus nerve compound action potentials," Acta Neurol Scand 110:232-238 (2004)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

The following articles, which are incorporated herein by reference, describe techniques using cuff electrodes to selectively excite peripheral nerve fibers distant from an electrode without exciting nerve fibers close to the electrode:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

One method used for selective stimulation is based on the observation that the stimulation/block threshold of fibers is inversely proportional to their radius. Thus, to stimulate only small fibers, all fibers are stimulated using a large cathodic current, and the large fibers are then blocked using a smaller anodal current, the net effect being action potential propagation in the small fibers only. To achieve unidirectional stimulation, one uses larger anodic currents on one side, thus blocking all fibers on that side. Because of the intrinsic physiological timescales of the ion channels in the axon, to block an action potential one uses a long pulse of approximately 1 millisecond. This long pulse may degrade stimulation efficiency. By comparison, an action potential can be triggered with pulses as short as approximately 10 microseconds.

A method for selective stimulation is described in Lertmanorat Z et al., "A novel electrode array for diameter-dependent control of axonal excitability: a simulation study," IEEE Transactions on Biomedical Engineering 51(7):1242-1250 (2004), which is incorporated herein by reference. The described Electrode Array Selective Stimulation (EASS) method relies on the structure of myelinated fibers and employs electrode arrays. The myelinated fibers are surrounded by a sheath of myelin, which functions as an isolator. In this sheath there are gaps at regular intervals, called nodes of Ranvier. The gap distance is roughly proportional to the radius of the axon. Ion channels are present only at these gaps.

The principle of EASS is that if an electric field is produced which is periodic along a nerve, and the period matches the gap distance of an axon with a certain diameter, then the axon essentially "sees" a constant electric field, so that no stimulation/block occurs. Axons of different gap-distances see a varying field and are thus stimulated/blocked. The variation in the electric field that an axon "sees" depends on the ratio between its gap distance and the field period. The variation also depends on the radial distance (depth) from the electrode to the axon. As the axon gets further away from the electrode, the field becomes less varying since the cathodic and anodal fields tend to cancel each other. The inventors of the present patent application estimate that the fields vary in a substantial manner up to a radial distance of about one period of the field. It should be noted that at all distances, the field has the same periodicity. Therefore, axons with a nodal gap distance which matches the field period will not be activated at any depth, but other axons may not be activated because the field becomes too weak.

Since the gap distance is proportional to the axon radius, by selecting a period for the field to change, a range of axon radii can be selected which are substantially not affected by the electric field. Setting the period of the field to be the gap distance of large fibers ensures that large fibers will not be affected by the stimulation. An advantage of this method for selective stimulation is that stimulus duration can be short; no blocking is needed since the large fibers are simply not activated.

An EASS electrode can be made by placing an alternating series of anode and cathodes along the axon, spaced a gap width apart. The cathodes and anodes can be ring shaped to give better field uniformity inside the nerve.

The main shortcoming of this method is that while it enables selective stimulation with short pulses, it does not provide unidirectional stimulation.

SUMMARY OF THE INVENTION

In some embodiments of the present invention, an electrode assembly for applying current to a nerve comprises at least one cathode, at least one anode, and two or more passive electrodes, which are fixed within a housing. The electrode assembly comprises a conducting element, typically a wire, which electrically couples the passive electrodes to one another. A "passive electrode," as used in the present application including the claims, is an electrode that is electrically "device-coupled" to neither (a) any circuitry that is electrically device-coupled to the at least one cathode or the at least one anode, nor (b) an energy source. "Device-coupled" means coupled, directly or indirectly, by components of a device, and excludes coupling via tissue of a subject. (It is noted that the passive electrodes may be passive because of a software-controlled setting of the electrode assembly, and that the software may intermittently change the setting such that these electrodes are not passive.) To "passively electrically couple," as used in the present application including the claims, means to couple using at least one passive electrode and no non-passive electrodes. The passive electrodes and conducting element create an electrical path for current that would otherwise leak outside the electrode assembly and travel around the outside of the housing through tissue of the subject.

For some applications, the at least one cathode and at least one anode are positioned within the housing longitudinally between the two or more passive electrodes. Alternatively, at least one of the passive electrodes is positioned between the at least one cathode and the at least one anode. For some applications, the electrode assembly is configured to apply unidirectional stimulation to the nerve. Alternatively or additionally, the electrode assembly is configured to selectively stimulate fibers of the nerve having certain diameters.

In some embodiments of the present invention, an electrode assembly for applying current to a nerve comprises two cathodes and at least one anode, which are fixed within a housing such that no anodes are positioned between the two cathodes. (If any anode is positioned between the two cathodes, then in at least one mode of operation, this anode applies no more than a trivial amount of anodal current to the nerve.) Typically, a distance between the two cathodes is equal to at least a radius of the nerve, e.g., at least 1.5 times the radius of the nerve. This electrode configuration creates a combined cathode having an activation function a peak of which has a magnitude less that of the anode, which results in unidirectional stimulation of the nerve in the direction of the cathodes. Typically, this electrode configuration also creates a virtual anode on the side of the cathodes opposite that of the anode, which results in selective fiber stimulation of fibers of the nerve having relatively small diameters. For some applications, the electrode assembly additionally comprises two or more passive electrodes coupled to one another, as described above, positioned such that the cathodes and the at least one anode are between the passive electrodes.

In some embodiments of the present invention, an electrode assembly for applying current to a nerve comprises a housing, which is placed in a vicinity of the nerve, one or more electrodes, fixed to the housing, and two longitudinally-elongated end insulating elements, fixed to the housing such that all of the electrodes are longitudinally between the insulating elements. Each of the end insulating elements has a length of at least 2 mm, such as at least 3 mm, or at least 4 mm. This elongation of the end insulating elements tends to lengthen the electrical path around the outside of the electrode assembly through tissue of the subject, thereby reducing the current that leaks from the assembly and flows through this path.

There is therefore provided, in accordance with an embodiment of the present invention, apparatus for applying current to a nerve, including:

a housing, adapted to be placed in a vicinity of the nerve;
at least one cathode and at least one anode, fixed to the housing;
two or more passive electrodes, fixed to the housing; and
a conducting element, which electrically couples the passive electrodes to one another.

In an embodiment, the two or more passive electrodes include exactly two passive electrodes.

In an embodiment, the at least one cathode and the at least one anode are fixed longitudinally between the two or more passive electrodes. Alternatively, at least one of the passive electrodes is fixed longitudinally between the at least one cathode and the at least one anode.

For some applications, the at least one anode includes one or more anodes which are configured to apply to the nerve an inhibiting current capable of inhibiting cathode-induced action potentials traveling in a non-therapeutic direction in the nerve. For some applications, the at least one cathode includes one or more cathodes which are configured to apply to the nerve a stimulating current, which is capable of inducing action potentials in a first set and a second set of nerve fibers of the nerve, and the at least one anode includes one or more anodes that are configured to apply to the nerve an inhibiting current, which is capable of inhibiting the induced action potentials in the second set of nerve fibers, the nerve fibers in the second set having generally larger diameters than the nerve fibers in the first set.

For some applications, the electrodes include ring electrodes. For some applications, the conducting element includes at least one passive element that impedes passage of current through the conducting element. For some applications, the housing includes one or more insulating elements that separate one or more of the at least one cathode, the at least one anode, and the passive electrodes, the insulating elements positioned closer to the nerve than are the at least one cathode, the at least one anode, and the passive electrodes.

There is also provided, in accordance with an embodiment of the present invention, apparatus for applying current to a nerve of a subject, including:

a housing, adapted to be placed in a vicinity of the nerve;
at least one cathode and at least one anode, fixed to the housing;
a passive electrode, fixed to the housing; and
a conducting element, which is electrically coupled to the passive electrode and extends to a remote location in a body of the subject at a distance of at least 1 cm from the housing.

There is further provided, in accordance with an embodiment of the present invention, apparatus for applying current to a nerve having a radius, including:

a housing, adapted to be placed in a vicinity of the nerve; and
two or more cathodes and one or more anodes, fixed to the housing such that no anodes are positioned longitudinally between the two or more cathodes.

In an embodiment, the apparatus includes two or more passive electrodes, fixed to the housing, such that the cathodes and the anodes are longitudinally between the passive electrodes; and a conducting element, which electrically couples the passive electrodes to one another.

For some applications, the two or more cathodes and the one or more anodes include ring electrodes. For some applications, the housing includes one or more insulating elements that separate one or more of the cathodes and the anodes, the insulating elements positioned closer to the nerve than are the cathodes and the anodes.

In an embodiment, the cathodes and anodes are fixed to the housing such that no cathodes are positioned longitudinally between the one or more anodes.

In an embodiment, the two or more cathodes are fixed to the housing at respective cathodic longitudinal locations, and are configured to apply to the nerve a stimulating current, which is capable of inducing action potentials in a first set and a second set of nerve fibers of the nerve; the one or more anodes are fixed to the housing at respective anodal locations, such that no cathodes are positioned longitudinally between the one or more anodes; the cathodes are configured to produce a virtual anode effect at a virtual anodal longitudinal site of the nerve, which is capable of inhibiting the induced action potentials in the second set of nerve fibers, the nerve fibers in the second set having generally larger diameters than the nerve fibers in the first set; and the cathodic locations are between (a) the anodal locations and (b) the virtual anodal site.

In an embodiment, the two or more cathodes are fixed to the housing at respective cathodic locations; the one or more anodes include a single anode, fixed to the housing at an anodal location; the anode is configured to produce a virtual cathode effect at a virtual cathodic longitudinal site of the nerve, which is incapable of generating action potentials in the nerve; and the anodal location is between (a) the cathodic locations and (b) the virtual cathodic site. Alternatively, the anode is configured to produce the virtual cathode effect at the virtual cathodic longitudinal site which does not generate action potentials in more than 10% of axons in the nerve.

In an embodiment, the cathodes are positioned such that a closest distance between two of the two or more cathodes is equal to at least the radius of the nerve, such as equal to at least 1.5 times the radius of the nerve.

In an embodiment, the cathodes are configured to apply respective cathodic currents to the nerve; the anodes are configured to apply respective anodal currents to the nerve; and for any given depth within the nerve, for a myelinated axon within the nerve of diameter less than 10 microns, the cathodic currents define, in combination, for the depth, a cathodic activation function having a maximum depolarizing amplitude, and the anodal currents define, in combination, for the depth, an anodal activation function having a maximum hyperpolarizing amplitude greater than the maximum depolarizing amplitude. For some applications, for a 1 micron diameter myelinated axon within the nerve, the maximum hyperpolarizing amplitude is greater than or equal to 110% of the maximum depolarizing amplitude.

There is still further provided, in accordance with an embodiment of the present invention, apparatus for applying current to a nerve, including:

a housing, adapted to be placed in a vicinity of the nerve;
one or more cathodes, fixed to the housing, and configured to apply respective cathodic currents to the nerve; and
one or more anodes, fixed to the housing, and configured to apply respective anodal currents to the nerve,
wherein, for any given depth within the nerve, for a myelinated axon within the nerve of diameter less than 10 microns, the cathodic currents define, in combination, for the depth, a cathodic activation function having a maximum depolarizing amplitude, and the anodal currents define, in combination, for the depth, an anodal activation function having a maximum hyperpolarizing amplitude greater than the maximum depolarizing amplitude.

For some applications, for a 1 micron diameter myelinated axon within the nerve, the maximum hyperpolarizing amplitude is greater than or equal to 110% of the maximum depolarizing amplitude.

In an embodiment, the one or more cathodes include two or more cathodes, fixed to the housing such that no anodes are positioned longitudinally between the two or more cathodes.

In an embodiment, the cathodes and anodes are fixed to the housing such that no cathodes are positioned longitudinally between the one or more anodes.

In an embodiment, the one or more cathodes are fixed to the housing at respective cathodic locations; the one or more anodes include a single anode, fixed to the housing at an anodal location; the anode is configured to produce a virtual cathode effect at a virtual cathodic longitudinal site of the nerve, which is incapable of generating action potentials in the nerve; and the anodal location is between (a) the cathodic locations and (b) the virtual cathodic site. Alternatively, the anode is configured to produce the virtual cathode effect at the virtual cathodic longitudinal site which does not generate action potentials in more than 10% of axons of the nerve.

There is yet further provided, in accordance with an embodiment of the present invention, apparatus for applying current to a nerve, including:

a housing, adapted to be placed in a vicinity of the nerve;
one or more electrodes, fixed to the housing; and
two elongated end insulating elements, fixed to the housing such that all of the electrodes are longitudinally between the insulating elements, and adapted to be disposed with respect to the nerve such that each of the end insulating elements has a length in a direction parallel with the nerve of at least 2 mm.

For some applications, each of the end insulating elements has a maximum thickness along at least 75% of its length of less than 0.5 mm. For some applications, the end insulating elements are adapted to be positioned closer to the nerve than are the electrodes. For some applications, the housing includes one or more internal insulating elements that separate one or more of the electrodes, the internal insulating elements being adapted to be positioned closer to the nerve than the electrodes.

For some applications, the length of each of the end insulating elements is at least 3 mm, or at least 4 mm.

There is also provided, in accordance with an embodiment of the present invention, a method for applying current to a nerve, including:

applying at least one cathodic current and at least one anodal current to the nerve; and
passively electrically coupling at least two longitudinal sites of the nerve to one another.

There is further provided, in accordance with an embodiment of the present invention, a method for applying current to a nerve of a subject, including:

applying at least one cathodic current and at least one anodal current to the nerve; and
passively electrically coupling at least one site of the nerve to a remote location in a body of the subject at a distance of at least 1 cm from the nerve.

There is still further provided, in accordance with an embodiment of the present invention, a method for applying current to a nerve having a radius, including:

applying two or more cathodic currents to the nerve at respective cathodic longitudinal sites; and
applying one or more anodal currents to the nerve at respective anodal longitudinal sites,
without applying anodal current to the nerve at any site longitudinally between the two or more cathodic longitudinal sites.

There is yet further provided, in accordance with an embodiment of the present invention, method for applying current to a nerve, including:

applying one or more cathodic currents to the nerve; and
applying one or more anodal currents to the nerve,
wherein, for any given depth within the nerve, for a myelinated axon within the nerve of diameter less than 10 microns, the cathodic currents define, in combination, for the depth, a cathodic activation function having a maximum depolarizing amplitude, and the anodal currents define, in combination, for the depth, an anodal activation function having a maximum hyperpolarizing amplitude greater than the maximum depolarizing amplitude.

There is also provided, in accordance with an embodiment of the present invention, a method for applying current to a nerve, including:

applying one or more currents to the nerve at respective longitudinal current-application sites of the nerve; and applying electrical insulation to the nerve at two longitudinal insulation sites of the nerve, wherein all of the current-application sites are longitudinally between the two insulation sites, and each of the insulation sites has a length in a direction parallel with the nerve of at least 2 mm.

There is additionally provided, in accordance with an embodiment of the present invention, a method, including:

applying, to a stimulation site of a nerve, a spatially-periodic stimulating field, configured to induce, in small fibers of the nerve, action potentials that propagate from the stimulation site towards a target site and away from the target site; and applying, to an inhibition site of the nerve, a spatially-periodic non-stimulating field, configured to partially depolarize at the inhibition site the small fibers of the nerve, without initiating action potentials therein, the partial depolarization of the small fibers being sufficient to inhibit the action potentials propagating away from the target site from continuing to propagate beyond the inhibition site, the stimulation site being between the target site and the inhibition site.

The present invention will be more fully understood from the following detailed description of embodiments thereof, taken together with the drawings, in which:

DETAILED DESCRIPTION OF EMBODIMENTS

Figure 1:
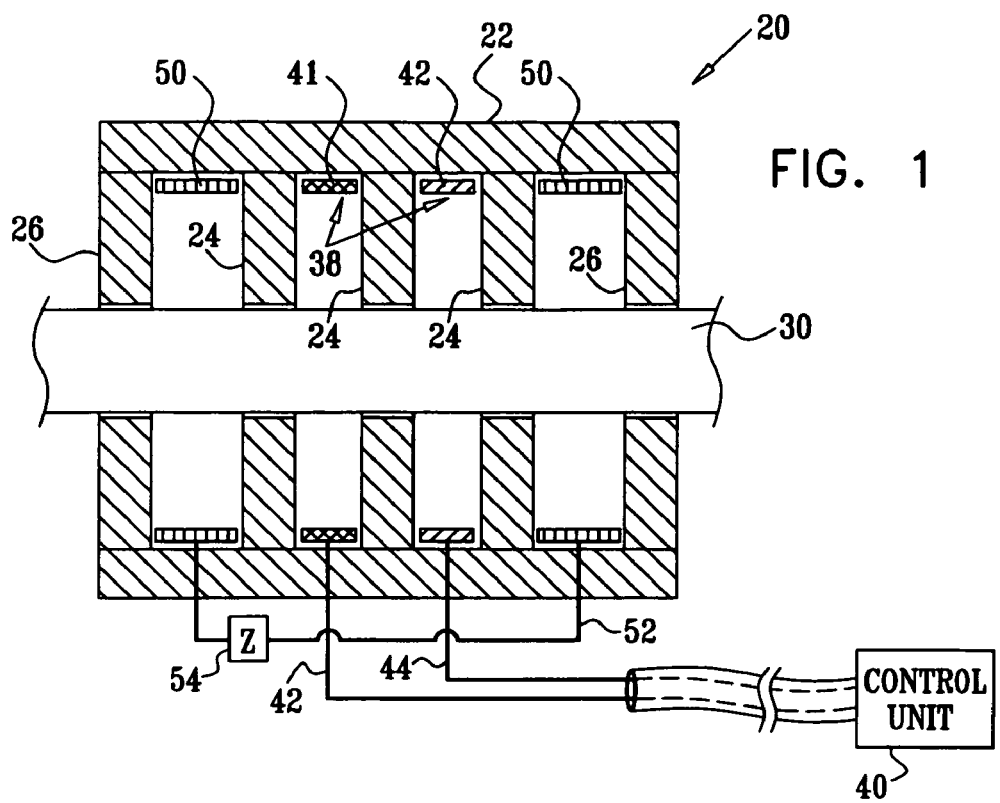
FIGS. 1-3 are schematic, cross-sectional illustration of electrode assemblies for applying current to a nerve, in accordance with respective embodiments of the present invention.

FIG. 1 is a schematic, cross-sectional illustration of an electrode assembly 20 for applying current to a nerve 30, in accordance with an embodiment of the present invention. It is noted that although the various electrode assemblies shown in the figures and described herein generally contain cylindrical configurations of their elements, other geometrical configurations, such as non-rotationally symmetric configurations, are also suitable for applying the principles of the present invention. In particular, a housing of the electrode assemblies (and the electrodes themselves) may form a complete circle around the nerve, or it may define an arc between approximately 0 and 90 degrees, between 90 and 180 degrees, between 180 and 350 degrees, or between 350 and 359 degrees around the nerve. For some applications, the electrode assemblies shown in the figures and described herein comprise electrodes that form rings around the nerve, and an insulating, elastic cuff that surrounds the electrodes.

Electrode assembly 20 comprises at least one active, i.e., stimulating and/or sensing, electrode 38, such as at least one cathode 41 and at least one anode 42. Each of these electrodes is fixed within a housing 22 of the electrode assembly. Active electrodes 38 are coupled to an implantable or external control unit 40 by leads 42 and 44. For some applications, active electrode configurations and/or stimulation techniques are used which are described in one or more of the patent applications incorporated by reference hereinbelow.

Electrode assembly 20 further comprises two or more passive electrodes 50, fixed within housing 22, and a conducting element 52, typically a wire, which electrically couples the passive electrodes to one another. The electrode assembly is configured such that the passive electrodes are electrically device-coupled, as defined hereinabove, to neither (a) any circuitry that is electrically device-coupled to the at least one cathode 41 or the at least one anode 42, nor (b) an energy source. Passive electrodes 50 and conducting element 52 create an electrical path for current that would otherwise leak outside electrode assembly 30 and travel around the outside of the housing through tissue of the subject.

For some applications, the active electrodes are positioned within housing 22 longitudinally between the two or more passive electrodes 50 (as shown in FIG. 1). Alternatively, at least one of the passive electrodes is positioned between the at least one cathode and the at least one anode (configuration not shown).

Internal insulating elements 24, which are either part of the body of the housing or affixed thereto, are typically placed so as to separate the electrodes, and to guide current from one of the electrodes towards the nerve prior to being taken up by another one of the electrodes. Typically (as shown), the insulating elements are closer to nerve 30 than are the electrodes. Alternatively (not shown), insulating elements 24 are generally flush with the faces of the electrodes. The electrode assembly typically further comprises one or more end insulating elements 26, which extend along nerve 30 in order to electrically isolate a portion of the nerve within housing 22 from a portion of the nerve outside the electrode assembly. The end insulating elements help direct any current that leaks from the active electrodes through the electrical path created by the passive electrodes and the conducting element. For some applications, conducting element 52 comprises at least one passive element 54, such as a resistor, capacitor, and/or inductor.

For some applications, the electrode assembly is configured to selectively stimulate fibers of the nerve having certain diameters, such as by using techniques described in one or more of the patent applications incorporated by reference hereinbelow. For example, control unit 40 may drive cathode 41 to apply to nerve 30 a stimulating current, which is capable of inducing action potentials in a first set and a second set of nerve fibers of the nerve, and drive anode 42 to apply to the nerve an inhibiting current, which is capable of inhibiting the induced action potentials traveling in the second set of nerve fibers, the nerve fibers in the second set having generally larger diameters than the nerve fibers in the first set.

For some applications, the electrode assembly is configured to apply unidirectional stimulation to the nerve, such as by using techniques described in one or more of the patent applications incorporated by reference hereinbelow. For example, control unit 40 may drive anode 42 to apply an inhibiting current capable of inhibiting device-induced action potentials traveling in a non-therapeutic direction in nerve 30.

For some applications, electrode assembly 20 comprises primary and secondary anodes, the primary anode located between the secondary anode and the cathode. The secondary anode is typically adapted to apply a current with an amplitude less than about one half an amplitude of a current applied by the primary anode.

In an embodiment of the present invention, electrode device 20 comprises one or more passive electrodes 50 which are not electrically device-coupled to one another. For some applications, the electrode device comprises exactly one passive electrode 50. A separate conducting element, typically a wire, is coupled to each passive electrode at a first end of the conducting element. The second end of the conducting element terminates at a relatively-remote location in the body of the subject that is at a distance of at least 1 cm, e.g., at least 2 or 3 cm, from electrode device 20. The remote location in the body thus serves as a ground for the passive electrode. For some applications, an electrode is coupled to the remote end of the conducting element, so as to increase electrical contact with tissue at the remote location.

Figure 2:
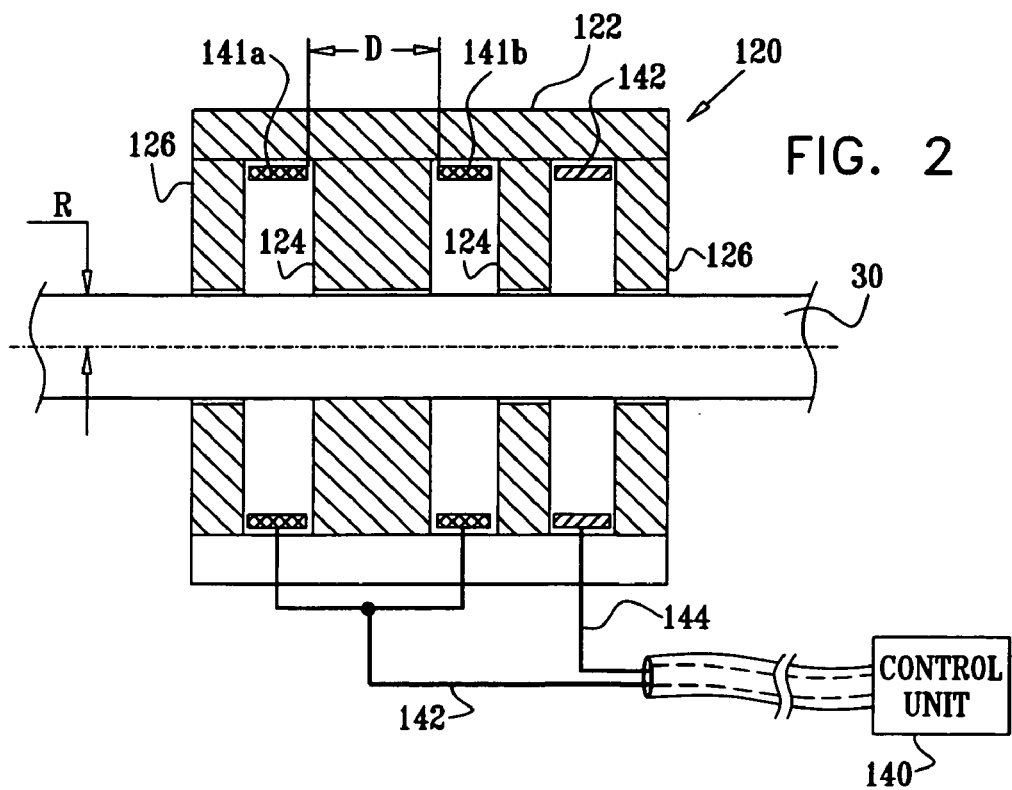

Reference is made to FIG. 2, which is a schematic, cross-sectional illustration of an electrode assembly 120 for applying current to nerve 30, in accordance with an embodiment of the present invention. Electrode assembly 120 comprises two cathodes 141a and 141b and at least one anode 142, which are fixed within a housing 122 such that no anodes are positioned between the two cathodes. Cathodes 141a and 141b are electrically coupled to one another, and are coupled to an implantable or external control unit 140 by a lead 142. Anode 142 is coupled to control unit 140 by a lead 144. Typically, a closest distance D between the two cathodes (i.e., the distance between the respective cathodes' edges that are closest to one another) is equal to at least a radius R of nerve 30, e.g., at least 1.5 times the radius of the nerve.

As described in detail hereinbelow with reference to FIGS. 4 and 5, this electrode configuration creates a combined cathode having an activation function a peak of which has a magnitude less than that of anode 142, which results in a stimulation that results in unidirectional propagation of action potentials in the nerve, in the direction going from anode 142 towards the cathodes. Typically, this electrode configuration also creates a virtual anode on the side of the cathodes opposite that of the anode, which results in selective fiber stimulation of fibers of the nerve having relatively small diameters.

Typically, electrode assembly 120 does not comprise any anodes on the side of the cathodes opposite anode 142 (i.e., the left side in the figures). However, for some applications, in which the virtual anode created on the side of the cathodes opposite the anode is not strong enough to create sufficient selective fiber stimulation, electrode assembly 120 comprises a second anode on the side of cathodes 141a and 141b opposite anode 142. A portion of the anodal current is driven through this anode in order to strengthen the blocking of larger-diameter fibers, thereby increasing the selection of the stimulation of small-diameter fibers. Typically, only a relatively small portion of the anodal current is driven through this second anode, in order to leave sufficient current for anode 142 to block all (or a very large portion of) action potentials generated by cathodes 141a and 141b (i.e., in order to preserve unidirectional stimulation).

For some applications, the electrode configuration of electrode assembly 120 is combined with electrode configurations and/or stimulation techniques described in one or more of the patent applications incorporated by reference hereinbelow.

Internal insulating elements 124, which are either part of the body of the housing or affixed thereto, are typically placed so as to separate the electrodes, and to guide current from one of the electrodes towards the nerve prior to being taken up by another one of the electrodes. Typically (as shown), the insulating elements are closer to nerve 30 than are the electrodes. Alternatively (not shown), insulating elements 124 are generally flush with the faces of the electrodes. The electrode assembly typically further comprises one or more end insulating elements 126, which extend along nerve 30 in order to electrically isolate a portion of the nerve within housing 122 from a portion of the nerve outside the electrode assembly.

Figure 3:
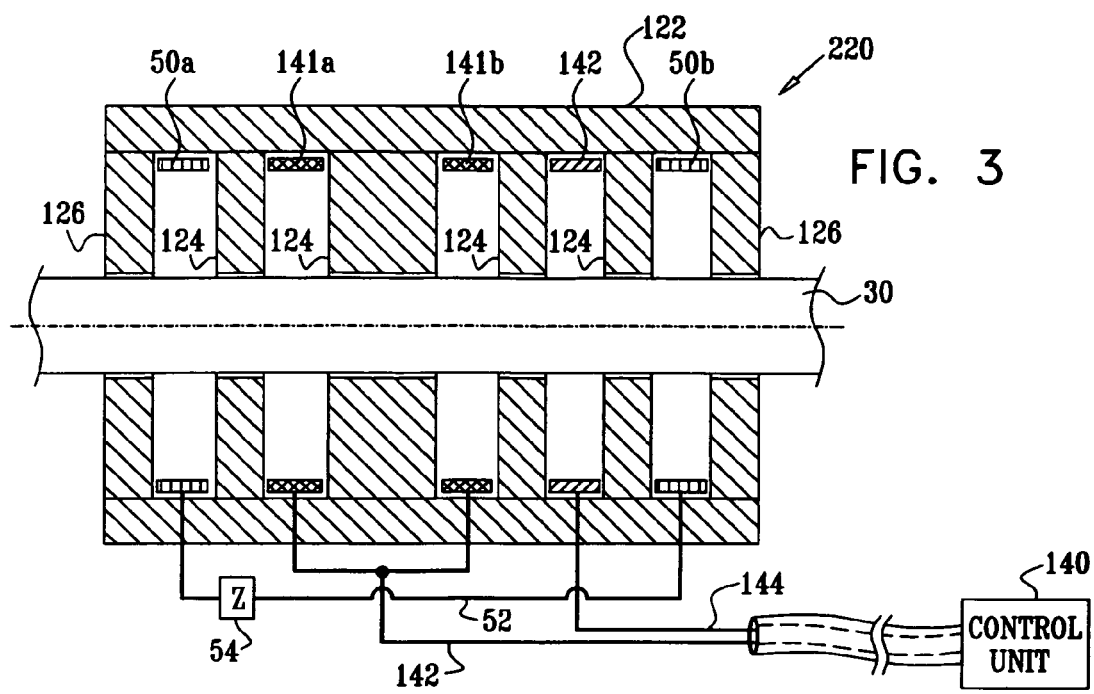

Reference is made to FIG. 3, which is a schematic, cross-sectional illustration of an electrode assembly 220 for applying current to nerve 30, in accordance with an embodiment of the present invention. Electrode assembly 220 is the same as electrode assembly 120, described hereinabove with reference to FIG. 2, except that electrode assembly 220 further comprises, on the ends thereof, two passive electrodes 50a and 50b and conducting element 52, as described hereinabove with reference to FIG. 1. Typically, a closest distance between anode 142 and passive electrode 50b is between about 0.7 mm and about 1 mm. Conducting element 52 optionally comprises passive element 54, as described hereinabove with reference to FIG. 1.

Figure 4:
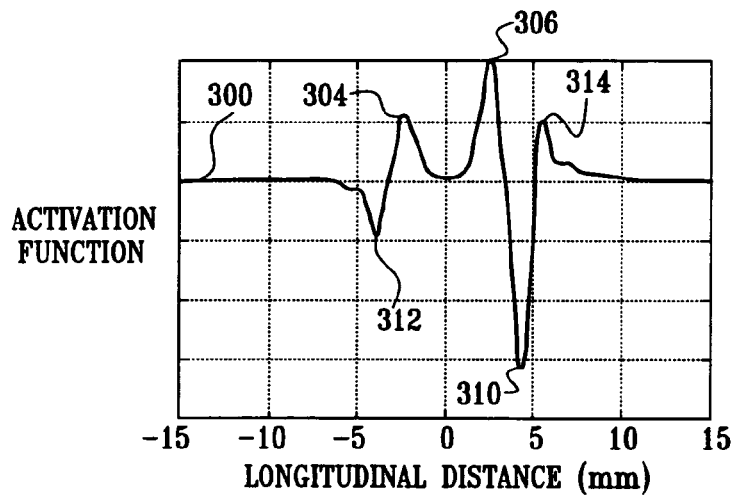
FIGS. 4 and 5 are graphs modeling calculated activation functions when current is applied using an electrode assembly similar to that of FIG. 3, in accordance with an embodiment of the present invention.
Figure 5:
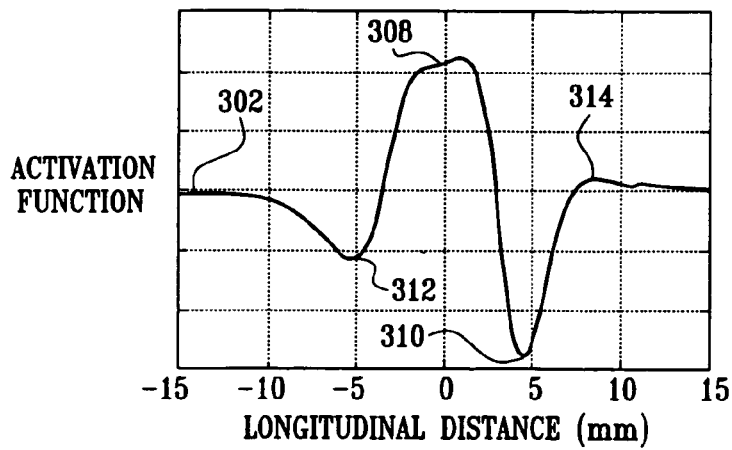

Reference is now made to FIGS. 4 and 5, which are graphs modeling calculated activation functions 300 and 302, respectively, of myelinated nerve fibers having a diameter of 1 micrometer, over a portion of the length of nerve 30, when current is applied using an electrode assembly similar to that shown in FIG. 3, in accordance with an embodiment of the present invention. For the purposes of modeling these activation functions, (a) cathodes 141a and 141b are placed at longitudinal sites on the nerve labeled z=−2 mm and z=2 mm, respectively, (b) anode 142 is placed at a longitudinal site z=4.1 mm, and (c) passive electrodes 50a and 50b are placed at longitudinal sites z=−4.1 mm and z=5.5 mm, respectively. All of the electrodes are placed at a radius of R=2.5 mm from the axis of nerve 30, which has a radius of 1.35 mm. Activation functions 300 (FIG. 4) and 302 (FIG. 5) are modeled at radii R=1.2 from the axis of nerve 30 (near the surface of the nerve) and R=0 (i.e., at the axis of the nerve), respectively.

Activation function 300 (FIG. 4) has two depolarization peaks 304 and 306, at approximately z=−2.5 and z=2.5, corresponding to the longitudinal positions of the two cathodes. In activation function 302 (FIG. 5), these two depolarization peaks have partially combined into a single, wide depolarization peak 308. Each of activation functions 300 and 302 has a hyperpolarization peak 310 at approximately z=4, corresponding to the longitudinal position of the anode. For a given fiber diameter (in this case, 1 micrometer), at all depths within the nerve, the amplitude of the hyperpolarization peak is greater than the amplitude of greatest depolarization peak, such as at least 10% or 20% greater. As a result, the hyperpolarization peak blocks propagation of substantially all cathode-induced action potentials traveling in the nerve from the cathode in the direction of the anode (i.e., to the right in the figures).

Each of activation functions 300 and 302 has a second, smaller hyperpolarization peak 312 at between about z=−4 and about z=−5, approximately corresponding to the longitudinal position of passive electrode 50a. This "virtual anode" effect, which is caused by cathodes 141a and 141b and passive electrode 50a, blocks propagation of almost all cathode-induced action potentials traveling in large- and medium-diameter fibers, but not those in small-diameter fibers, resulting in selective small-diameter fiber activation in the direction from cathode 141a to passive electrode 50a (i.e., to the left in the figures). It is noted that in the absence of passive electrode 50a (in the embodiment described with reference to FIG. 2), the two-cathode configuration still results in the virtual anode effect between about z=−4 and about z=−5. Current flows through tissue around the outside of the electrode assembly, rather than between the passive electrodes via conducting element 52.

Activation functions 300 and 302 additionally have a second, smaller depolarization peak 314 at between about z=6 and z=8, approximately corresponding to the longitudinal position of passive electrode 50b. This "virtual cathode" effect, which is caused by anode 142 and passive electrode 50b, does not generate action potentials in more than 10% of axons of nerve 30 (or does not generate action potentials in any axons of nerve 30) because of the virtual cathode's relatively low amplitude, and its vicinity to strong hyperpolarization peak 310.

It is noted that if cathodes 141a and 141b are positioned at a closest distance D less than radius R of nerve 30 (FIG. 2), the cathodes begin to behave as a single cathode, generating a depolarization peak having a greater amplitude than those in activation functions 300 and 302. As a result, the amplitude of hyperpolarization peak 310 is no longer greater than the amplitude of the greatest depolarization peak at all nerve fiber diameters. The stimulation is thus not unidirectional at all nerve fiber diameters.

Figure 6:
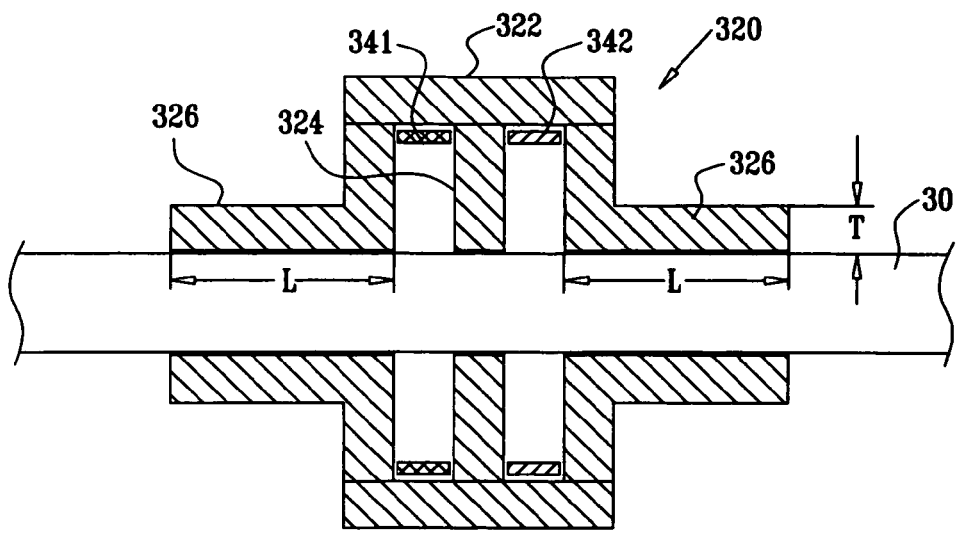
FIG. 6 is a schematic, cross-sectional illustration of another electrode assembly for applying current to a nerve, in accordance with an embodiment of the present invention.

Reference is made to FIG. 6, which is a schematic, cross-sectional illustration of an electrode assembly 320 for applying current to nerve 30, in accordance with an embodiment of the present invention. Electrode assembly 320 comprises one or more electrodes, such as at least one cathode 341 and at least one anode 342, which are fixed within a housing 322. Electrode assembly 320 further comprises two elongated end insulating elements 326, which are either part of the body of the housing or affixed thereto. The end insulating elements extend along nerve 30 in order to electrically isolate a portion of the nerve within housing 322 from a portion of the nerve and other tissue outside the electrode assembly. Each of the end insulating elements has a length L of at least 2 mm, such as at least 3 mm, or at least 4 mm. This elongation of the end insulating elements tends to lengthen the electrical path around the outside of the electrode assembly through tissue of the subject, thereby reducing the current that leaks from the assembly and flows through this path.

For some applications, the insulating elements have a thickness T along at least 75% of their length of less than about 0.5 mm. For some applications, at least one internal insulating element 324, which is either part of the body of the housing or affixed thereto, is placed so as to separate the electrodes, and to guide current from one of the electrodes towards the nerve prior to being taken up by another one of the electrodes.

Figure 7:
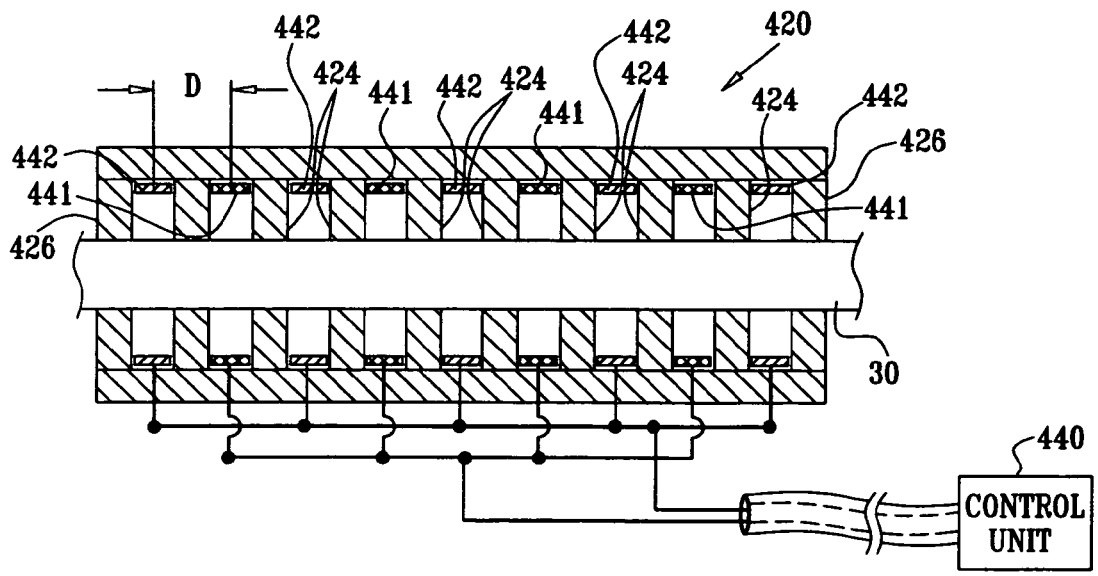
FIG. 7 is a schematic, cross-sectional illustration of an electrode assembly for applying Electrode Array Selective Stimulation (EASS) to a nerve, in accordance with an embodiment of the present invention.

Reference is made to FIG. 7, which is a schematic, cross-sectional illustration of an electrode assembly 420 for applying Electrode Array Selective Stimulation (EASS) to nerve 30, in accordance with an embodiment of the present invention. EASS assembly 420 comprises alternating anodes 442 and cathodes 441. Typically, five anodes 442 and four cathodes 441 are adequate to create a periodic electric field along a sufficiently long length of nerve. A control unit 440 is configured to drive the electrodes of EASS assembly 420 to apply a spatially-periodic field to nerve 30 that is configured to target fibers of a selected diameter, as described in the Background of the Invention section hereinabove.

Internal insulating elements 424, which are either part of the body of the housing or affixed thereto, are typically placed so as to separate the electrodes, and to guide current from one of the electrodes towards the nerve prior to being taken up by another one of the electrodes. Typically (as shown), the insulating elements are closer to nerve 30 than are the electrodes. Alternatively (not shown), insulating elements 424 are generally flush with the faces of the electrodes. The electrode assembly typically further comprises one or more end insulating elements 426, which extend along nerve 30 in order to electrically isolate a portion of the nerve within the housing from a portion of the nerve outside the electrode assembly.

Figure 8:
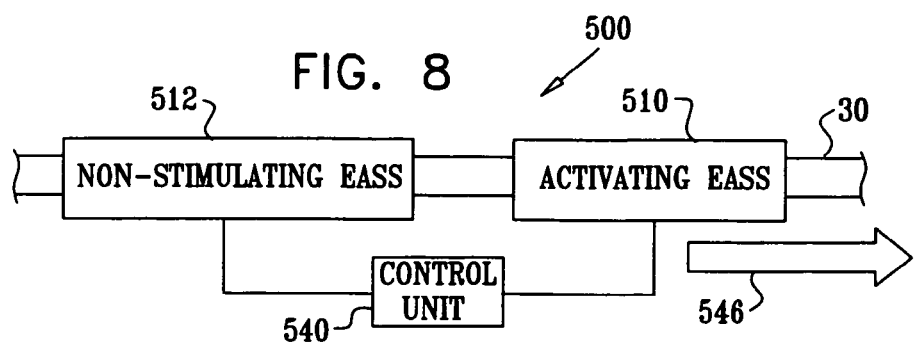
FIG. 8 is a schematic illustration of a selective stimulation EASS system, in accordance with an embodiment of the present invention.

Reference is made to FIG. 8, which is a schematic illustration of a selective stimulation EASS system 500, in accordance with an embodiment of the present invention. EASS system 500 comprises two EASS assemblies 420 (FIG. 7), and a control unit 540 electrically coupled to both assemblies. The control unit, at any given time, configures one of the assemblies to function as an activating EASS assembly 510, and the other to function as a non-stimulating EASS assembly 512. (Alternatively, one of the assemblies is permanently configured to function as activating EASS assembly 510, and the other is permanently configured to function as non-stimulating EASS assembly 512.)

Control unit 540 drives activating EASS assembly 510 to apply a spatially-periodic stimulating field to nerve 30, and configures the field to induce, in small fibers of the nerve, action potentials that propagate towards a target site (in the direction indicated by an arrow 546) and away from the target site. The control unit also drives non-stimulating EASS assembly 512 to apply a spatially-periodic non-stimulating field, and to configure the field to partially depolarize the small fibers of the nerve, without initiating action potentials therein or in larger fibers of the nerve. The partial depolarization of the small fibers is sufficient to inhibit the action potentials generated by activating EASS assembly 510 in a direction opposite the target site from continuing to propagate beyond the inhibition site of non-stimulating EASS assembly 512. As a result, unidirectional small-diameter fiber stimulation is achieved towards the target site (i.e., in the direction indicated by arrow 546). Both the stimulating and non-stimulating fields are typically applied using short pulses, e.g., pulses having a duration of between about 10 and about 100 microseconds. The amplitude of the stimulating pulses is typically between about 0.5 and about 15 mA, depending on the number of fibers to be activated, and the amplitude of the non-stimulating pulses is typically between about 0.1 and about 5 mA, depending on the number of fibers to be blocked. During each application of stimulation, the non-stimulating field is typically applied slightly before application of the stimulating field, e.g., between about 500 and about 0 microseconds earlier.

Application of the non-stimulating field by non-stimulating EASS assembly 512 causes a partial depolarization of the target axons, which causes some of the ion channels in the axons to begin their gating cycles. However, the non-stimulating field is configured so to minimize the likelihood of causing depolarization sufficient to trigger an action potential. As a result of the partial depolarization, a portion of the ion channels enter their refractory periods. When a stimulating field is subsequently applied, these channels cannot begin the gating cycle. As a result, the number of channels available is insufficient to trigger an action potential. The fibers are therefore unable to transmit action potentials.

Typically, the field applied by non-stimulating EASS assembly 512 is configured to partially depolarize only small fibers, by using the EASS selective-fiber-diameter stimulation techniques described hereinabove.

It is noted that the triggering thresholds of axons vary based on the axons' diameters. Thus, a pulse of a magnitude sufficient to partially depolarize small fibers may trigger action potentials in large-diameter fibers. Therefore, without the use of the EASS partial depolarization techniques described herein, application of a conventional depolarizing pulse causes undesired complete depolarization (i.e., action potential generation) in large-diameter fibers, in addition to the desired partial depolarization of small-diameter fibers.

Alternatively, for some applications, applying the non-stimulating field comprises applying a non-EASS non-stimulating pulse, at a strength sufficient to cause partial depolarization of target axons, but insufficient to trigger an action potential.

For some applications, EASS system 500 comprises a single long EASS electrode assembly. The non-stimulating pulse is applied by a portion (e.g., about half) of the electrode assembly on the side thereof further from the target direction. The stimulating pulse is applied by the remaining portion (e.g., the other half) of the electrode assembly on the side thereof closer to the target direction. Alternatively, the stimulating pulse is applied by the entire electrode assembly, or any sufficiently long portion thereof. Use of the entire electrode device for applying the stimulating pulse generally results in a more periodic field having a lower current density.

In an embodiment of the present invention, EASS system 500 is configured to perform unidirectional stimulation of a human vagus nerve. The system is configured to selectively activate only A-delta fibers, while not activating A fibers. In the human vagus nerve, the conduction velocity of A and A-delta fibers is about 20 m/sec and about 8 m/sec, respectively (see Evans M S et al., cited hereinabove). These velocities imply nodal gaps of 0.5 mm and 0.2 mm, respectively. The inter-electrode distance D between the respective centers of the electrodes (FIG. 7) is thus typically about 0.5 mm, which enables excitation of A-delta fibers up to a depth from the nerve surface of approximately 0.5 mm. For a human vagus nerve with a diameter of about 2.5 mm, these fibers constitute about 75% of the fibers in the bundle, assuming that they are uniformly scattered throughout the bundle. The length of a single EASS electrode with five anodes and four cathodes (as shown in FIG. 7) is typically less than about 1 cm, and two such electrodes are readily placed side-by-side on a human vagus nerve.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. Provisional Patent Application 60/383,157 to Ayal et al., filed May 23, 2002, entitled, "Inverse recruitment for autonomic nerve systems,"

International Patent Application PCT/IL02/00068 to Cohen et al., filed Jan. 23, 2002, entitled, "Treatment of disorders by unidirectional nerve stimulation," and U.S. patent application Ser. No. 10/488,334, in the national stage thereof, U.S. patent application Ser. No. 09/944,913 to Cohen and Gross, filed Aug. 31, 2001, entitled, "Treatment of disorders by unidirectional nerve stimulation," which issued as U.S. Pat. No. 6,684,105, U.S. patent application Ser. No. 09/824,682 to Cohen and Ayal, filed Apr. 4, 2001, entitled "Method and apparatus for selective control of nerve fibers,"

U.S. patent application Ser. No. 10/205,475 to Gross et al., filed Jul. 24, 2002, entitled, "Selective nerve fiber stimulation for treating heart conditions,"

U.S. patent application Ser. No. 10/205,474 to Gross et al., filed Jul. 24, 2002, entitled, "Electrode assembly for nerve control," which issued as U.S. Pat. No. 6,907,295, International Patent Application PCT/IL03/00431 to Ayal et al., filed May 23, 2003, entitled, "Selective nerve fiber stimulation for treating heart conditions,"

International Patent Application PCT/IL03/00430 to Ayal et al., filed May 23, 2003, entitled, "Electrode assembly for nerve control," and U.S. patent application Ser. No. 10/529,149, in the national stage thereof, U.S. patent application Ser. No. 10/719,659 to Ben David et al., filed Nov. 20, 2003, entitled, "Selective nerve fiber stimulation for treating heart conditions,"

U.S. patent application Ser. No. 11/022,011 to Cohen et al., filed Dec. 22, 2004, entitled, "Construction of electrode assembly for nerve control," and U.S. patent application Ser. No. 11/234,877 to Ben-David et al., filed Sep. 22, 2005, entitled, "Selective nerve fiber stimulation."

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for applying current to a nerve, comprising:
   a control unit;
   a housing, adapted to be placed in a vicinity of the nerve;
   at least one cathode and at least one anode, fixed to the housing, and electrically device-coupled to the control unit;
   two or more passive electrodes, fixed to the housing; and
   a conducting element, which electrically couples the passive electrodes to one another,
   wherein the control unit and passive electrodes are configured such that each of the passive electrodes is electrically device-coupled to neither (a) any circuitry that is electrically device-coupled to the at least one cathode or the at least one anode, nor (b) an energy source.

2. The apparatus according to claim 1, wherein the two or more passive electrodes comprise exactly two passive electrodes.

3. The apparatus according to claim 1, wherein the at least one cathode and the at least one anode are fixed longitudinally between the two or more passive electrodes.

4. The apparatus according to claim 1, wherein at least one of the passive electrodes is fixed longitudinally between the at least one cathode and the at least one anode.

5. The apparatus according to claim 1, wherein the at least one anode comprises one or more anodes which are configured to apply to the nerve an inhibiting current capable of inhibiting cathode-induced action potentials traveling in a non-therapeutic direction in the nerve.

6. The apparatus according to claim 1, wherein the at least one cathode comprises one or more cathodes which are configured to apply to the nerve a stimulating current, which is capable of inducing action potentials in a first set and a second set of nerve fibers of the nerve, and wherein the at least one anode comprises one or more anodes that are configured to apply to the nerve an inhibiting current, which is capable of inhibiting the induced action potentials in the second set of nerve fibers, the nerve fibers in the second set having generally larger diameters than the nerve fibers in the first set.

7. The apparatus according to claim 1, wherein the electrodes comprise ring electrodes.

8. The apparatus according to claim 1, wherein the conducting element comprises at least one passive element that impedes passage of current through the conducting element, the passive element selected from the group consisting of: a resistor, a capacitor, and an inductor.

9. The apparatus according to claim 1, wherein the housing comprises one or more insulating elements that separate one or more of the at least one cathode, the at least one anode, and the passive electrodes, the insulating elements positioned closer to the nerve than are the at least one cathode, the at least one anode, and the passive electrodes.

* * * * *

UNITED STATES PATENT AND TRADEMARK OFFICE
CERTIFICATE OF CORRECTION

PATENT NO. : 7,627,384 B2 Page 1 of 1
APPLICATION NO. : 11/280884
DATED : December 1, 2009
INVENTOR(S) : Ayal et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 998 days.

Signed and Sealed this

Second Day of November, 2010

David J. Kappos
*Director of the United States Patent and Trademark Office*